Figure 1A:
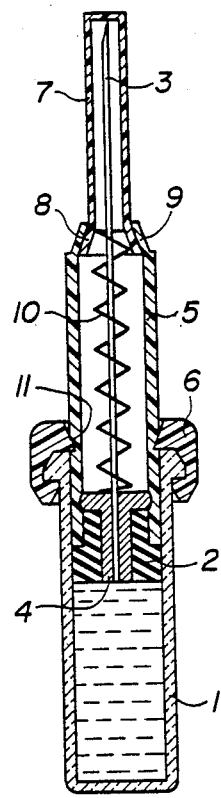

United States Patent [19]

Verlier

[11] Patent Number: 4,936,830
[45] Date of Patent: Jun. 26, 1990

[54] PREFILLED SYRINGE

[76] Inventor: Jacques Verlier, 16, rue Michel-Servet, 1206 Geneve, Switzerland

[21] Appl. No.: 216,774

[22] Filed: Jul. 8, 1988

[30] Foreign Application Priority Data

Jul. 10, 1987 [CH] Switzerland .......................... 2635/87

[51] Int. Cl.$^5$ .............................................. A61M 5/178
[52] U.S. Cl. .................................... 604/110; 604/195; 604/198
[58] Field of Search ...................... 604/187, 192–198, 604/231, 235, 236, 240, 244, 110, 263

[56] References Cited

U.S. PATENT DOCUMENTS 3,306,290 2/1967 Weltman ............................. 604/197
3,587,575 6/1971 Lichtenstein ...................... 604/195
4,795,432 1/1989 Karczmer ......................... 604/198
4,838,863 6/1989 Allard et al. ....................... 604/195

Primary Examiner—Stephen C. Pellegrino
Attorney, Agent, or Firm—Woodard, Emhardt, Naughton Moriarty & McNett

[57] ABSTRACT

A prefilled syringe is disclosed which comprises a syringe body with a slidable piston defining a compartment therein containing a substance to be injected. An injection needle is arranged for communicating with said compartment through said piston and sleeve means are provided around the needle in slidable relationship with said syringe body. A compression spring is urging the sleeve means in a position in which the same surround the tip of the needle and the syringe body is closed before and after an injection.

12 Claims, 3 Drawing Sheets

PREFILLED SYRINGE

The present invention relates to a prefilled syringe and in particular to a syringe provided with protection means for the needle thereof.

The general object of the invention is to provide a prefilled syringe which can be used, for example, for vaccinating, and which consists of a complete and ready for use unit of a simple and economic structure, while ensuring a high level of safety during all the steps of its use. A further object of the invention is to provide such a syringe which is substantially non-reusable.

For this purpose, the syringe according to the invention comprises a syringe body; a slidable piston inside said syringe body defining a compartment therein containing a substance to be injected; an injection needle capable of communicating with said compartment through said piston; telescopic sleeve means arranged around at least the tip portion of said needle in slidable relationship with said syringe body; and compression spring means arranged around said needle between said sleeve means and said piston.

More particularly, the syringe according to the invention comprises a hollow syringe body closed at one of its ends and open at the other end; a piston slidably mounted inside the syringe body and defining between the closed end of the syringe body and the piston a compartment containing a substance to be injected; an injection needle, the base of which is fastened to a needle support member, said support member and said piston being adapted for allowing at least partial insertion of said support member in said piston and for allowing the needle to communicate with said syringe body compartment upon such insertion; a substantially cylindrical sleeve member which is open at both ends, said needle support member being mounted at one end portion of said sleeve member, retaining means for fastening said sleeve member to the syringe body during the storage of the prefilled syringe and at least until the beginning of the injection; a substantially cylindrical protective sheath member for protecting the needle, said sheath member being closed at one end to surround the tip of the needle by a wall capable of being punctured by the needle, while the other end of said sheath member extends through an opening of said sleeve member and is slidably engaged therein; and a coil spring which surrounds a portion of the needle and abuts at one end against said needle support member and at its other end against said protective sheath member to urge the same into a rest position where said sheath member protrudes outside said sleeve member and surrounds the needle tip.

According to a preferred embodiment, said retaining means consist of an elastic collar supported by a circular flange formed around the open end of said syringe body, said collar being provided with at least one inward lip arranged to engage a peripheral circular groove in the outer wall surface of said sleeve member.

The cross section of said groove in said sleeve member and said inward lip of said collar can be shaped so that said collar opposes the pushing back of the sleeve member inside the syringe body under the effect of a force exerted in the axial direction on the syringe, as long as this force does not slightly exceed the value of the force needed to puncture said protective sheath member and to drive the needle against the action of said coil spring in the flesh of a subject, whereas, when said force becomes slightly stronger than said value, said collar allows said sleeve member to slide inside the syringe body.

In an alternate solution, the cross section of said groove in said sleeve member and said inward lip of said collar are shaped so as to maintain said sleeve member and said syringe body in their mutual position, and said needle support member is detachably mounted inside said end portion of said sleeve member.

According to another preferred embodiment, the syringe of the invention comprises valve means arranged between the needle and the compartment containing the substance to be injected, so as to allow said compartment to communicate with the needle only during the injection. Said valve means can comprise a solid ball-like member disposed in a hollow space inside said piston, said space being arranged in a passage extending through the piston, so as to provide a seat for said ball-like member and urge said member elastically against said seat to obturate said passage in a rest position of said ball-like member, said needle support member being arranged to push away said ball-like member from said seat upon insertion of said needle support member into said piston, thus opening said passage through the piston.

As it will become apparent from the following description, the syringe according to the invention has the advantages of being very easy to handle and of comprising protective means for the needle, which are part of the syringe itself and which are arranged in such a manner that the needle is exposed only during the injection, while it is automatically retracted to the protected position after the injection. Accordingly, the syringe offers an excellent guarantee of sterility before its use and eliminates the risk of contamination due to a person being accidentally pricked after an injection, as it was possible with the usual syringes.

Other advantages and features of the syringe according to the invention will become more readily apparent from the description of different embodiments given hereafter by way of example, with reference to the accompanying drawings, in which:

FIGS. 1(a) to 1(d) show a first embodiment;
FIGS. 2(a) to 2(c) show a second embodiment, and
FIGS. 3(a) to 3(e) show another version of the first embodiment.

As shown in FIGS. 1(a) to 1(d), the syringe comprises a cylindrical hollow syringe body 1, which is open at one of its ends and closed at the other to form a compartment for the liquid substance to be injected. The syringe body 1 is advantageously constituted by a glass tube, but could of course be made from any other suitable material, for example a metal or a synthetic resin.

A piston 2 is mounted inside the syringe body 1 for low friction sliding engagement of its outer side wall—or of sealing means fastened thereto—with the inner wall of the syringe body 1, while maintaining the tightness of the above mentioned compartment defined by the syringe body and the back wall of the piston 2 facing the closed end of the syringe body.

An injection needle 3 is supported with its tip pointing in the direction opposite to that of the closed end of the syringe body 1 and its rear end held in a substantially cylindrical support member 4 which maintains the needle base aligned with the axis of the syringe body 1. The rear end of the needle 3 communicates with the compartment containing the substance to be injected, via a passage extending through the piston 2. More specifically, in the embodiment shown in FIG. 1, the support member 4 of the needle has a cylindrical portion inserted in and extending axially through the piston 2, which portion contains a channel, for example the channel of the needle itself, constituting said passage.

Figure 1B:
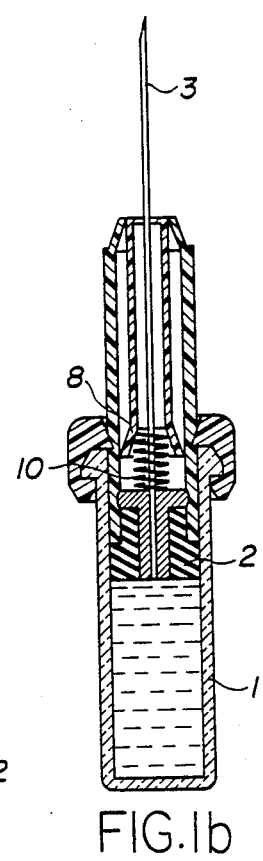
Figure 1C:
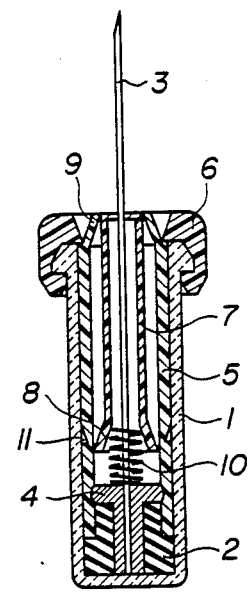

A cylindrical sleeve 5, which is open at both ends and which has an outer diameter slightly smaller than the inner diameter of the syringe body 1, is positioned, in the initial storage condition shown in FIG. 1(a), with one of its ends located along the body 1, the sleeve 5 being secured against motion with respect to the body 1 by means of a retaining collar 6 made of an elastic material, for example rubber or a resilient plastic material. The collar 6 is held by means of a circular flange placed around the open end of the syringe body 1, and it can be removed for the initial filling of the syringe with the substance to be injected. Further, the collar 6 has a lip on its inside to engage a peripheral circular groove 11 formed perpendicularly to the axis of the syringe in the outer side of the sleeve wall 5. In the case of the embodiment shown in FIGS. 1(a) to 1(d), the rear side of the groove 11 in the sleeve 5 is perpendicular to the axis of the sleeve and the front side of the groove is at a slight angle with respect to that axis. The effect of this particular shape of the groove 11 on the mode of operation of the syringe will be explained later in the description.

Figure 1D:
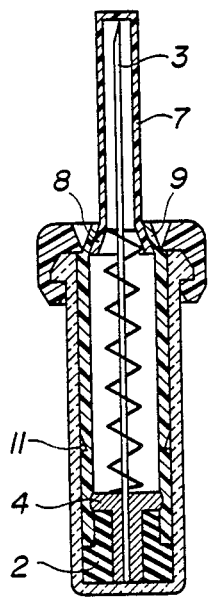
Figure 2A:
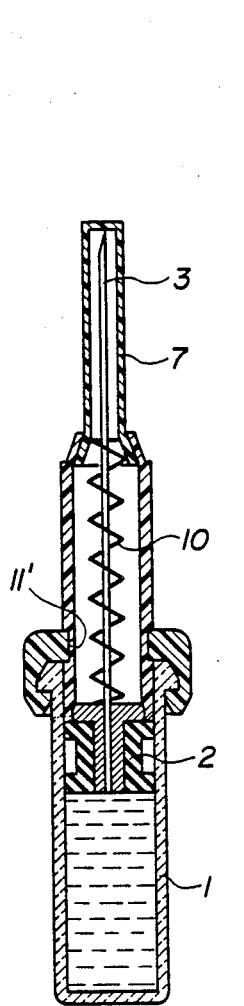
Figure 2B:
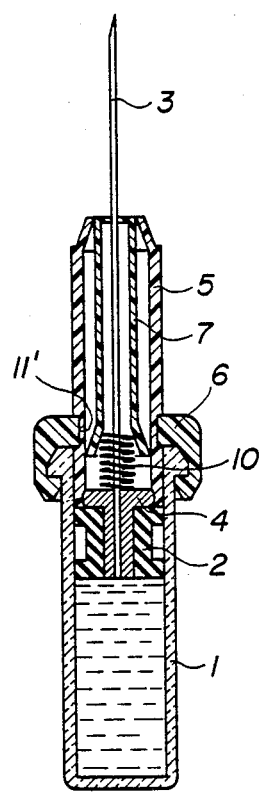
Figure 2C:
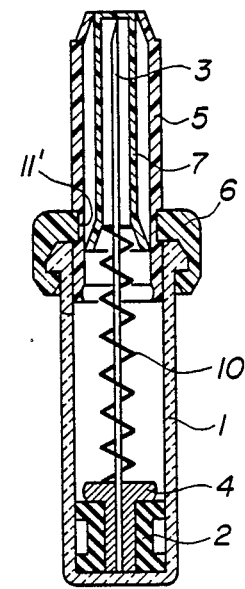

A protective sheath 7 surrounds the forward end of the needle 3 in the initial and final positions shown, respectively, in FIGS. 1(a) and 1(d). This sheath consists of a substantially cylindrical sleeve which has an outer diameter smaller than the inner diameter of the sleeve 5 and which is closed at its forward end by a wall forming a cap easily punctured by the tip of the needle. The sheath is open on its rear and arranged inside the sleeve 5 and has a truncated end portion 8 widening at the rear to provide an abutment and a sealing portion cooperating with a truncated seat 9 of corresponding shape and size at the forward end of the sleeve 5.

A coil spring 10 working under compression surrounds the needle 3, one end of the spring abutting against the support member 4 and the other end against the inner face of the truncated end portion 8 of the sheath 7 so as to urge the truncated portion 8 against the seat 9 in the positions shown in FIGS. 1(a) and 1(d). In these positions, the inside of the sleeve 5 is practically tight against the outside, and in the initial rest position shown in FIG. 1(a), the elastic force of the spring 10 is sufficient to prevent the needle 3 from puncturing the end wall of the sheath 7 under normal conditions before the syringe is used. The support member 4 comprises a front portion disposed inside the sleeve 5 and fastened thereto. More specifically, the edge of this portion of the support member 4 fits into a circular groove formed in the inner wall of the sleeve 5.

In accordance with this embodiment, the operation of the syringe is as follows:

As a first step, the forward end of the protecting sheath 7 of the needle is placed against the skin of the subject to whom the injection is to be administered and a pressure is applied to the syringe body 1. At a certain value of the pressure on the sheath 7, the same is caused to retract inside the sleeve 5 and to compress the spring 10, with the result that the needle 3 punctures the end wall of the sheath 7 immediately after the initiation of the movement and begins to penetrate inside the subject's flesh. However, the injection does not begin before the needle has reached its position of maximum penetration shown in FIG. 1(b). In this position, the protective sheath 7 is entirely retracted inside the sleeve 5 and the spring 10 is fully compressed. It should be noted that during the penetration of the needle between the positions shown in FIGS. 1(a) and 1(b), respectively, the needle 3 is perfectly well guided in the axial direction, by the hole punctured by the needle tip through the forward wall of the sheath 7, the edge of the rear truncated portion 8 of the sheath 7 being axially guided by the inner wall of the sleeve 5.

The second step of operation of the syringe, during which the injection takes place, occurs between the positions shown in FIGS. 1(b) and 1(c). The application of a pressure on the syringe body 1 is continued after the position shown in FIG. 1(b) has been reached, which results in the inner edge of the lip of the collar 6 being pushed out from the peripheral groove 11 owing to the low inclination of the front side of the groove, thereby allowing the syringe body 1 to move forward while the sleeve remains stationary. Accordingly, the sleeve 5 is sliding backward into the syringe body 1 and the piston 2 is pushed towards the bottom of the syringe body 1, thereby causing the injecting of the liquid substance until a position is reached, as illustrated in FIG. 1(c), where the injection is completed, with the bottom of the syringe body 1 abutting against the piston 2 and the sleeve 5 driven wholly inside the syringe body 1.

When the injection is thus completed and the syringe pulled backwards to remove the needle from the flesh of the subject, the spring 10 expands to push the protective sheath 7 outside the sleeve into the position shown in FIG. 1(d). The sleeve 5 remains inside the syringe body 1 with the piston 2 against its bottom, the inside lip of the collar 6 abutting against an edge surrounding the rear of the truncated forward end 9 of the sleeve 5, thus retaining the latter inside the syringe body 1. In this final position, the truncated rear portion 8 of the protective sheath 7 abuts against the seat 9 of the sleeve 5, and the sheath 7 surrounds completely the tip of the needle 3, which eliminates any risk of accidental pricking.

Preferably, the needle support member 4 and the piston 2 are arranged so as to be held together relatively loosely, the piston 2 itself not being fastened directly to the sleeve 5. Accordingly, the piston 2 is capable of being separated from the support member 4 as well as from the sleeve 5, the piston remaining at the bottom of the syringe body 1 when one tries to remove the sleeve 5 and the needle 3 from the syringe 1. This structure thus renders an attempt to reuse the syringe very difficult.

In a second embodiment of the syringe as shown in FIGS. 2(a) to 2(c), a peripheral groove 11' formed in the outer face of the sleeve wall 5 to receive the retaining collar 6, has in cross-section two sides perpendicular to the sleeve axis 5. In this case, the syringe body 1 and the sleeve 5 are maintained together by the collar 6 during the injection operation. Further, the support member 4 is fastened to the piston 2, but is retained only loosely inside the sleeve 5. This causes the injection to be carried out in an automatic mode, i.e. through the sole action of the spring 10, during retraction of the needle.

The operation of the syringe according to this second embodiment is as follows:

The needle is driven into the flesh and the protective sheath 7 retracts inside the sleeve 5 in a way similar to that of the first embodiment, until the position shown in FIG. 2(b) is reached, which corresponds to the position illustrated in FIG. 1(b). At this moment, the spring is fully compressed and the elastic force it exerts becomes higher than the retention force which maintains the support element 4 fastened to the sleeve 5. The support member 4 is thus pushed towards the bottom of the cylindrical body 1 under the action of the spring 10, pulling the piston 2 therewith. The inner volume defined by the piston 2 and the bottom of the syringe body 1 decreases accordingly, and the liquid is injected through the needle 3 until the final position shown in FIG. 2(c) is reached. This final position is similar to that shown in FIG. 1(d) except that the sleeve 5 does not retract inside the syringe body 1, but surrounds the sheath 7.

During the injection, the needle is progressively retracted and the injection is thus not made at a constant depth, but at progressively decreasing depth. This can be an advantage by providing a diffusion of the substance to be injected in a larger region.

The embodiment of the syringe shown in FIGS. 3(a) to 3(e) is similar to that of FIGS. 1(a) to 1(d), except that it further comprises valve means arranged between the needle 3 and the compartment containing the substance to be injected, these valve means being arranged so that the needle and this compartment only communicate during the injection.

Figure 3E:
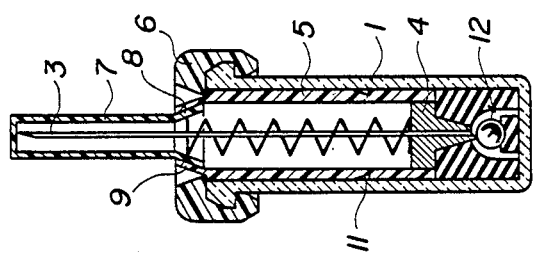
Figure 3D:
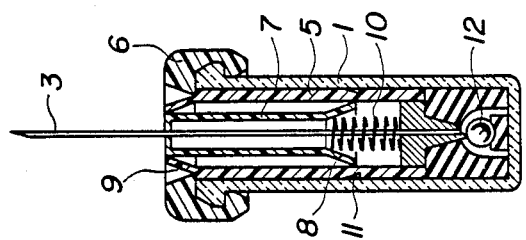
Figure 3C:
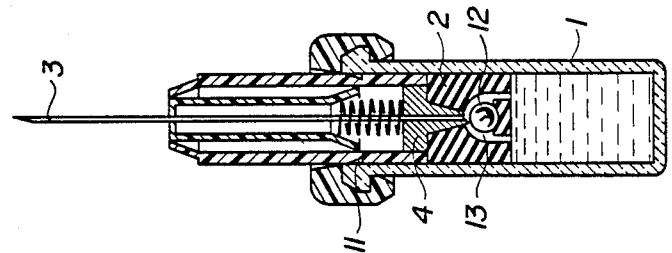
Figure 3B:
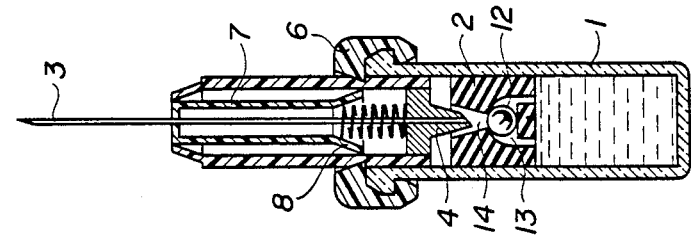
Figure 3A:
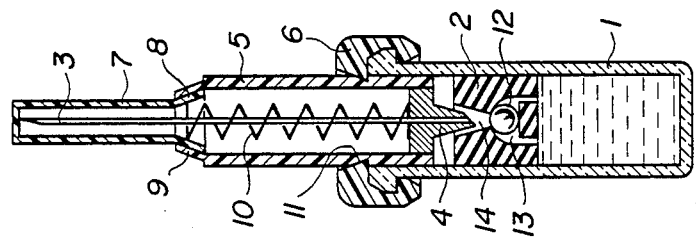

More specifically, these valve means comprise a solid ball 12, made from any appropriate material, for example metal, glass or a plastic material, and placed inside the piston 2 in a hollow space 13 provided in a passage 14 through the piston. In the initial position shown in FIG. 3(a) as well as in the fully protracted position of the needle and the retracted position of the protective sheath 7 inside the sleeve 5 shown in FIG. 3(b), the piston 2 is separated from the needle support member 4 and the ball 12 is pressed against a seat formed at the opening of the passage 14 into the hollow space 13, thus obturating this opening by the effect of the elastic force resulting from the pressure exerted by an inner portion of the piston opposite the seat. The support member 4 has a rear portion through which extends the needle 3. As shown in FIG. 3(c), when the inside lip of the retaining collar 6 is forced out from the groove 11 through the pushing action exerted on the syringe body 1, the syringe body moves forward together with the piston 2 until the piston comes in contact with the support member 4, the rear portion of which enters the passage 14 to abut against the ball 12 and to remove it from the valve seat of the passage 14. The compartment containing the substance to be injected is then communicating with the needle 3. The tip of the rear portion of the support member 4 is bevelled as shown in FIGS. 3(a) to 3(e) to leave the lower end of the needle free. The injection is then started, and continued between the positions shown in FIGS. 3(c) and 3(d). The operation of the syringe according to this last embodiment is otherwise similar to that of the embodiment of FIGS. 1(a) to 1(d), of which it is another version. Identical or similar components in all figures have been designated by the same reference numerals.

We claim:

1. A prefilled syringe comprising a hollow syringe body closed at one of its ends and open at the other end; a piston slidably mounted inside the syringe body and defining between the closed end of the syringe body and the piston a compartment containing a substance to be injected; an injection needle, the base of which is fastened to a needle support member, said support member and said piston being adapted for allowing at least partial insertion of said support member in said piston and for allowing the needle to communicate with said syringe body compartment upon such insertion; a substantially cylindrical sleeve member which is open at both ends, said needle support member being mounted at one end portion of said sleeve member; retaining means for fastening said sleeve member to the syringe body during the storage of the prefilled syringe and at least until the beginning of the injection; a substantially cylindrical protective sheath member for protecting the needle, said sheath member being closed at one end to surround the tip of the needle by a wall capable of being punctured by the needle, while the other end of said sheath member extends through an opening of said sleeve member and is slidably engaged therein; and a coil spring which surrounds a portion of the needle and abuts at one end against said needle support member and at its other end against said protective sheath member to urge the same into a rest position where said sheath member protrudes outside said sleeve member and surrounds the needle tip.

2. A syringe according to claim 1, wherein said retaining means consist of an elastic collar supported by a circular flange formed around the open end of said syringe body, said collar being provided with at least one inward lip arranged to engage a peripheral circular groove in the outer wall surface of said sleeve member.

3. A syringe according to claim 2, wherein the cross section of said groove in said sleeve member and said inward lip of said collar are shaped so that said collar opposes the pushing back of the sleeve member inside the syringe body under the effect of a force exerted in the axial direction on the syringe, as long as this force does not slightly exceed the value of the force needed to puncture said protective sheath member and to drive the needle against the action of said coil spring in the flesh of a subject, whereas, when said force becomes slightly stronger than said value, said collar allows said sleeve member to slide inside the syringe body.

4. A syringe according to claim 2, wherein the cross section of said groove in said sleeve member and said inward lip of said collar are shaped so as to maintain said sleeve member and said syringe body in their mutual position, and wherein said needle support member is detachably mounted inside said end portion of said sleeve member.

5. A syringe according to claim 1, comprising valve means arranged between the needle and the compartment containing the substance to be injected, so as to allow said compartment to communicate with the needle only during the injection.

6. A syringe according to claim 5, wherein said valve means comprise a solid ball-like member disposed in a hollow space inside said piston, said space being arranged in a passage extending through the piston, so as to provide a seat for said ball-like member and urge said member elastically against said seat to obturate said passage in a rest position of said ball-like member, said needle support member being arranged to push away said ball-like member from said seat upon insertion of said needle support member into said piston, thus opening said passage through the piston.

7. A prefilled syringe comprising a hollow syringe body closed at one of its ends and open at the other end; a piston slidably mounted inside the syringe body and defining between the closed end of the syringe body and the piston a compartment containing a substance to be injected; an injection needle, the base of which is fastened to a needle support member, said support member and said piston being adapted for allowing at least partial insertion of said support member in said piston and for allowing the needle to communicate with said syringe body compartment upon such insertion; telescopic sleeve means arranged around at least the tip portion of said needle in slidable relationship with said syringe body; and compression spring means arranged around said needle between said sleeve means and said piston.

8. A prefilled syringe comprising a hollow syringe body closed at one of its ends and open at the other end; an piston slidably mounted inside the syringe body and defining between the closed end of the syringe body and the piston compartment containing a substance to be injected; an injection needle, the base of which is fastened to a needle support member, said support member being inserted into said piston so as to allow the needle to communicate with said syringe body compartment; telescopic sleeve means arranged around at least the tip portion of said needle in slidable relationship with said syringe body; and compression spring means arranged around said needle between said sleeve means and said piston.

9. A prefilled syringe comprising a hollow syringe body closed at one of its ends and open at the other end; a piston slidably mounted inside the syringe body and defining between the closed end of the syringe body and the piston a compartment containing a substance to be injected; an injection needle, the base of which is fastened to a needle support member, said support member being inserted into said piston so as to allow the needle to communicate with said syringe body compartment; a substantially cylindrical sleeve member which is open at both ends, said needle support member being mounted at one end portion of said sleeve member; retaining means for fastening said sleeve member to the syringe body during the storage of the prefilled syringe and at least until the beginning of the injection; a substantially cylindrical protective sheath member for protecting the needle, said sheath member being closed at one end to surround the tip of the needle by a wall capable of being punctured by the needle, while the other end of said sheath member extends through an opening of said sleeve member and is slidably engaged therein; and a coil spring which surrounds a portion of the needle and abuts at one end against said needle support member and at its other end against said protective sheath member to urge the same into a rest position where said sheath member protrudes outside said sleeve member and surrounds the needle tip.

10. A syringe according to claim 9, wherein said retaining means consist of an elastic collar supported by a circular flange formed around the open end of said syringe body, said collar being provided with at least one inward lip arranged to engage a peripheral circular groove in the outer wall surface of said sleeve member.

11. A syringe according to claim 10, wherein the cross section of said groove in said sleeve member and said inward lip of said collar are shaped so that said collar opposes the pushing back of the sleeve member inside the syringe body under the effect of a force exerted in the axial direction on the syringe, as long as this force does not slightly exceed the value of the force needed to puncture said protective sheath member and to drive the needle against the action of said coil spring in the flesh of a subject, whereas, when said force becomes slightly stronger than said value, said collar allows said sleeve member to slide inside the syringe body.

12. A syringe according to claim 10, wherein the cross section of said groove in said sleeve member and said inward lip of said collar are shaped so as to maintain said sleeve member and said syringe body in their mutual position, and wherein said needle support member is detachably mounted inside said end portion of said sleeve member.

* * * * *

UNITED STATES PATENT AND TRADEMARK OFFICE
CERTIFICATE OF CORRECTION

PATENT NO. : 4,936,830

DATED : June 26, 1990

INVENTOR(S) : Jacques Verlier

It is certified that error appears in the above-identified patent and that said Letters Patent is hereby corrected as shown below:

In column 2, lines 56-57, please delete the word "wal-l" and insert in lieu thereof the word --wall--.

In column 3, line 36, please delete the word "and" and insert in lieu thereof the word --end--.

Signed and Sealed this

Twenty-fifth Day of June, 1991

Attest:

HARRY F. MANBECK, JR.

*Attesting Officer*   *Commissioner of Patents and Trademarks*